US011931356B1

(12) United States Patent
Androphy et al.

(10) Patent No.: US 11,931,356 B1
(45) Date of Patent: Mar. 19, 2024

(54) COMPOSITIONS AND METHODS FOR TREATING HUMAN PAPILLOMA VIRUS INFECTIONS

(71) Applicants: THE TRUSTEES OF INDIANA UNIVERSITY, Indianapolis, IN (US); KOVINA THERAPEUTICS INC., Indianapolis, IN (US)

(72) Inventors: Elliot J. Androphy, Indianapolis, IN (US); Samy O. Meroueh, Carmel, IN (US); Zhijian Lu, Indianapolis, IN (US)

(73) Assignees: The Trustees of Indiana University, Indianapolis, IN (US); Kovina Therapeutics, Inc., Indianapolis, IN (US)

( * ) Notice: Subject to any disclaimer, the term of this patent is extended or adjusted under 35 U.S.C. 154(b) by 0 days.

(21) Appl. No.: 18/060,391

(22) Filed: Nov. 30, 2022

(51) Int. Cl.
| | | |
|---|---|---|
| *A61K 31/496* | (2006.01) | |
| *A61K 9/51* | (2006.01) | |
| *A61K 31/517* | (2006.01) | |
| *A61K 31/519* | (2006.01) | |

(52) U.S. Cl.
CPC .............. *A61K 31/496* (2013.01); *A61K 9/51* (2013.01); *A61K 31/517* (2013.01); *A61K 31/519* (2013.01)

(58) Field of Classification Search
CPC .. A61K 31/496; A61K 31/517; A61K 31/519; A61K 9/51
See application file for complete search history.

(56) References Cited

U.S. PATENT DOCUMENTS

| | | |
|---|---|---|
| 7,019,000 B1 | 3/2006 | Bernard |
| 2009/0274621 A1 | 11/2009 | Wegrzyn |
| 2010/0105722 A1 | 4/2010 | Kuehnert |
| 2016/0214994 A1 | 7/2016 | Yingli |
| 2020/0197369 A1 | 6/2020 | Tang |

FOREIGN PATENT DOCUMENTS

WO 2021/212010 10/2021

OTHER PUBLICATIONS

Tan, et al., Cutaneous B-human papillomavirus E6 proteins bind Mastermind-like coactivators and repress Notch signaling, Proceedings of the National Academy of Sciences of the United States of America, 109(23), E1473-E1480, SE1473/1-SE1473/2 (2012) (Year: 2012).*
Krist et al. "Catalytically Important Residues of E6AP Ubiquitin Ligase Identified Using Acid-Cleavable Photo-Cross-Linkers". Biochemistry. 2015. 54(29): pp. 4411-4414.
Scheffner et al. "Identification of a human ubiquitin-conjugating enzyme that mediates the ES-AP-dependent ubiquitination of p53", Proc. Natl. Acad. Sci. USA. 1994. vol. 91, pp. 8797-8801.
PubChem-SID-132887069, Modify Date: May 31, 2019 (May 31, 2019).
International Search Report for PCT/US21/27746.
STN registry compound RN#1048824-05-0 (Entry date Sep. 12, 2008).

* cited by examiner

*Primary Examiner* — Erich A Leeser
(74) *Attorney, Agent, or Firm* — Barnes & Thornburg LLP

(57) ABSTRACT

The invention provides compositions, compounds, formulations, and methods for treating HPV infections including pre-malignant infections and cancer. Compounds that covalently bind to the HPV E6 protein are disclosed.

13 Claims, 13 Drawing Sheets

Specification includes a Sequence Listing.

1                                                   51
MFQDPQERPRKLPQLCTELQITIRDIILECVYCKQQLLRREVYDFAFRDLCIVYRDGNPYAVCD

KCLKFYSKISEYRHYCYSLYGTTLEQQYNKPLCDLLIRCINCQKPLCPEEKQRHLDKKQRFHNI
                              151
RGRWTGRCMSCCRSSRTRRETQL

Fig. 1

CYS51

DMSO

E6 (C51S)

DMSO

Compound 1

Compound 2

CYS51

E6 (C51S)

Compound 3

CYS51

E6 (C51S)

Compound 4

CYS51

E6 (C51S)

Compound 5

CYS51

E6 (C51S)

Compound 6

CYS51

E6 (C51S)

Compound 7

Compound 8

E6 (C51S)

Compound 9

CYS51

E6 (C51S)

SEQUENCE LISTING

```
Sequence total quantity: 1
SEQ ID NO: 1            moltype = AA  length = 151
FEATURE                 Location/Qualifiers
source                  1..151
                        mol_type = protein
                        organism = Human papilloma virus type 16
SEQUENCE: 1
MFQDPQERPR KLPQLCTELQ TTIHDIILEC VYCKQQLLRR EVYDFAFRDL CIVYRDGNPY   60
AVCDKCLKFY SKISEYRHYC YSLYGTTLEQ QYNKPLCDLL IRCINCQKPL CPEEKQRHLD  120
KKQRFHNIRG RWTGRCMSCC RSSRTRRETQ L                                 151
```

COMPOSITIONS AND METHODS FOR TREATING HUMAN PAPILLOMA VIRUS INFECTIONS

GOVERNMENT RIGHTS

This invention was made with government support under TR001108 awarded by the National Institutes of Health. The government has certain rights in the invention.

FIELD OF THE INVENTION

The invention relates to compounds, formulations, and methods for treating human papillomavirus infections.

SEQUENCE LISTING

This application contains a sequence listing which has been submitted in eXtensible Markup Language (XML) format via the Patent Center and is hereby incorporated by reference in its entirety. The XML-formatted sequence listing, created on Nov. 7, 2022 is named KOVI-002-00US-ST26 and is 2 kilobytes in size.

BACKGROUND

Human papillomavirus (HPV) constitutes a group of more than 200 subtypes that are common worldwide. These viruses are sub-grouped into mucosal and cutaneous HPVs according to their ability to infect the mucosa or the skin of genital or upper respiratory tracts. HPV types fall into two groups, low risk and high risk, for their association with cancer and precursor lesions. Persistent infection of high-risk HPV types carries a high risk of progression from pre-malignant to invasive and metastatic cervical, anogenital and oropharyngeal cancers. A few low-risk HPV types can cause warts on or around the genitals, anus, mouth, or throat. There are approximately 14 high-risk HPV types. Of all, HPV 16 is known to be the most common oncogenic type. Both men and women can become infected with HPV and develop HPV-caused cancers.

HPV infection is a well-established cause of cervical cancer and is a relevant factor in other anogenital (anus, vulva, vagina and penis) cancers as well as head and neck cancers. HPV is also responsible for other diseases such as recurrent juvenile respiratory papillomatosis and genital warts, both mainly caused by HPV types 6 and 11. Cancer of the cervix is the 4th most common cancer among women worldwide with an estimated 604,127 new cases and 341,831 deaths in 2020. HPV types 16 and 18 are together responsible for approximately 70% of all cervical cancer cases worldwide.

Currently, there is no effective medical therapy for women and men infected with HPV. While most infections are benign, standard remedies such as surgery, chemotherapy, and radiation are painful and have complications and co-morbidities. Prophylactic HPV vaccines can only reduce or prevent new infections. For that approach to be effective and ultimately reduce the incidence of HPV associated malignancies, the vaccine must be administered pre-infection, and the rates of vaccine uptake must be high. Unfortunately, vaccine coverage in both developed and developing countries has been suboptimal, with less than 50% coverage in most regions across the globe. While prophylactic HPV vaccines are highly effective, they are not therapeutic and therefore have no utility in patients with existing infections or HPV-induced cancers. For example, for patients in a recurrent, persistent, and metastatic infection category of cervical cancer, the five-year survival rate is less than 5%. Therefore, new infections remain significant, constitute a substantial cause of morbidity worldwide, and place a considerable burden on health and medical systems.

SUMMARY

The invention discloses compounds that covalently bond to cysteine 51 (Cys51) in the E6AP binding pocket of the HPV E6 protein, thus preventing E6 from binding to an E6AP protein. Preventing HPV E6 from binding to E6AP inhibits the subsequent p53 ubiquitination cascade that may lead to cancer. Thus, the invention provides therapeutic compounds that are covalent irreversible inhibitors of HPV E6 useful for treating HPV infections. In specific embodiments, compounds of the invention include an acrylamide substituent that facilitates the Cys51 covalent bonding.

HPV-16 is the etiological agent for about half of all cervical dysplasias and cancers, and the vast majority of HPV E6 associated cancers of the anogenital and oral mucosa. E6 is essential for viral genome replication and targets the p53 protein for intracellular destruction as well as other activities. The E6 protein is a major transforming protein of many types of papillomaviruses. The p53 protein is the dominant cell cycle regulator. In epithelial tumors induced by high-risk mucosal HPVs, including human cervical carcinoma and a growing number of head-and-neck cancers, p53 is degraded by HPV E6 binding to E6AP. In E6-mediated degradation of p53, HPV E6 proteins interact with the LxxLL motif of E6AP. A subsequent conformational change in E6AP-bound E6 exposes a large p53 interaction surface to generate the E6•E6AP•p53 trimeric complex. In this stable trimeric complex, the E6AP ubiquitin ligase is catalytically activated and/or is close enough to tag p53 with ubiquitin molecules for degradation by the ubiquitin-proteasome system. The ubiquitination and degradation of p53 leaves the cell devoid of the ability to induce apoptosis, cell cycle arrest, DNA damage sensing, and the resulting suppression of tumorigenesis.

The effect can be reversed in HPV-driven tumor cells by reduced expression of HPV E6, which reactivates p53 expression and leads to senescence or apoptosis. However, inhibition of HPV E6 has achieved only partial success. The unique topography of the α-helix binding groove of HPV E6 is essential in maintaining strong polar contacts with the HPV E6 binding motif. The rim arginines R10, R55, R102, R129, and R131 form multiple hydrogen bonds with both backbone and side-chain atoms. However, rather than using electrostatic intermolecular interactions such as hydrogen-bonding and π-cation contacts, or ionic bonds as forming the basis for interaction with HPV E6, compounds of the invention selectively and covalently bond to Cysteine in the E6AP binding pocket of the HPV E6 protein. In HPV-16 E6, this cysteine is at position 51 (Cys51, FIG. 1). This covalent bonding interferes with the activities of HPV E6 including its ability to interact with E6AP. Protein-ligand binding typically occurs by intermolecular forces such as ionic bonds, hydrogen bonds, and Van der Waals forces. Therefore, measurably irreversible covalent bonding between a ligand and a target molecule is atypical. The E6AP binding pocket on HPV E6 acts as a "hot spot" for association with cellular proteins encoding the LxxLL motif. The compounds disclosed herein covalently bind at the Cys51 residue within this pocket, or "hot spot" in HPV E6 and irreversibly block its interactions with E6AP, thus preventing p53 ubiquitination and degradation. This also interferes with other binding partners that encode the HPV E6 binding motif. In specific embodiments, compounds disclosed herein include an acrylamide substituent. Thus, covalent bonding of the compounds to the Cys51 residue of the HPV-16 E6 protein occurs via this acrylamide substituent.

Aspects of the invention provide compounds that form a covalent bond with Cys51 in a human papilloma virus 16 HPV E6 protein, thereby preventing binding of the HPV E6 protein to an E6AP protein.

In another aspect, the invention provides for a formulation comprising a compound that forms a covalent bond with Cys51 in a human papilloma virus 16 HPV E6 protein, thereby preventing binding of the HPV E6 protein to an E6AP protein.

In some embodiments, the formulation comprises a pharmaceutically-acceptable adjuvant, diluent or carrier. Additionally or alternatively, the formulation is provided in a nanoparticle for targeted delivery.

In other aspects, the invention provides a method for treating an HPV infection, the method comprising the step of delivering a formulation comprising a compound that forms a covalent bond with a Cys51 residue in a human papilloma virus 16 HPV E6 protein, thereby preventing binding of the HPV E6 protein to an E6AP protein.

In some embodiments of the methods, the formulation is delivered orally, transdermally, topically, subcutaneously, intramuscularly, or intravenously. In some embodiment, formulations of the invention are prepared for topical application to the cervix, anus, or pharynx. In further embodiments, formulations of the invention comprise an effective dose for transdermal delivery of about 0.01% to about 10% of a compound that forms a covalent bond with Cys51 in a human papilloma virus 16 HPV E6 protein, thereby preventing binding of the HPV E6 protein to an E6AP protein.

Alternatively, formulations of the invention are prepared as time-release formulations, in some embodiments. In other embodiments, the formulations inhibit E6AP binding to HPV E6, thus preventing ubiquitination of p53.

In some embodiments formulations further comprises a compound selected from the group consisting of fatty acids, glucose, amino acids, cholesterol, lipids, glycosides, alkaloids, and natural phenols.

BRIEF DESCRIPTION OF THE DRAWINGS

FIG. 1 provides the amino acid sequence of the HPV-16 E6 protein (SEQ ID NO: 1) and indicates the position of amino acid cysteine 51 (Cys51) in the HPV-16 E6 protein sequence as referenced herein.

DETAILED DESCRIPTION

Figure 2A:
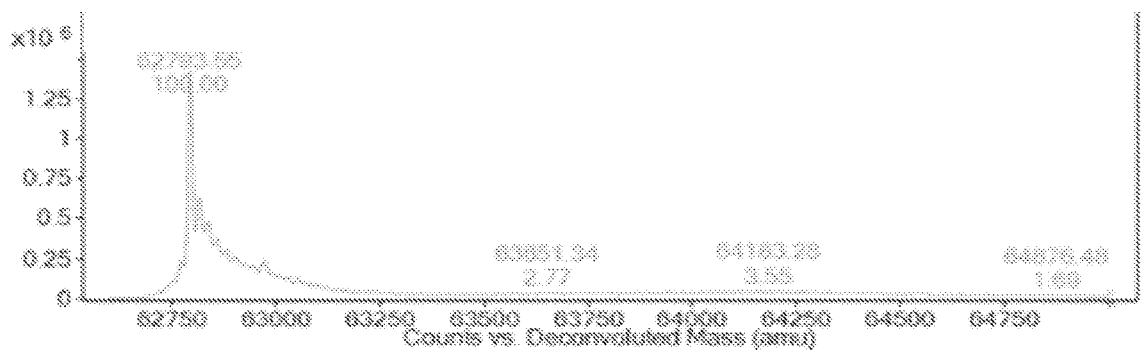
FIGS. 2A and 2B show control mass spectra for the HPV-16 E6 protein with Cys51 (FIG. 2A) and C51S (cysteine 51 mutation to serine in the HPV-16 E6 protein, FIG. 2B).

The invention provides therapeutic compounds, formulations, and methods for treating HPV infections. Particularly, the invention provides compounds that are covalent and irreversible inhibitors of HPV E6. Compounds of the invention covalently bond to the amino acid, cysteine 51 (Cys51), in the HPV-16 E6 protein thereby preventing E6 from binding to an E6AP protein. Preventing HPV E6 from binding to E6AP inhibits the p53 ubiquitin cascade that results in a disruption in cell cycle regulation. In specific embodiments, compounds disclosed herein include an acrylamide substituent. Thus, covalent bonding of the compounds to the Cys51 residue of the HPV-16 E6 protein occurs via this acrylamide substituent.

The oncogenicity of HPV is associated with its high-risk oncoproteins, E6 and E7. For example, HPV E6 immortalizes human mammary epithelial cells and the E6 proteins of the high-risk HPVs cooperate with the HPV E7 protein to immortalize primary human keratinocytes. The p53 tumor-suppressor protein regulates the cell cycle and hence functions as a major suppressor of tumorigenesis. In epithelial tumors induced by high-risk mucosal HPVs, including human cervical carcinoma and a growing number of head-and-neck cancers, p53 is degraded by HPV E6. E6AP ubiquitin-protein ligase is the founding member of the HECT ubiquitin ligase family, and is involved in targeting proteins for degradation within cells.

The E6 protein is a major transforming protein of many types of papillomaviruses. HPV E6 is an approximately 150-amino acid protein comprising two intrinsically disordered termini and tandem repeat domains connected by a helical linker. HPV E6 effects an oncogenic phenotype by functionally inactivating various cellular antitumor proteins through protein-protein interactions (PPIs) using an alpha-helix groove interface for binding. HPV E6 interacts with a multitude of host cellular proteins such as p53, E6AP, E6BP, Ada3, MAML1, etc. and proteins containing PDZ domains. HPV E6 itself can alter apoptosis through both p53-dependent and p53-independent pathways.

Aspects of the invention provide compounds that form a covalent bond with the cysteine amino acid residue in a specific binding pocket of the HPV E6 protein or so-called E6AP binding pocket, thereby preventing binding of another protein in the binding pocket.

FIG. 1 provides the amino acid sequence of the HPV-16 E6 protein (SEQ ID NO: 1) and indicates the position of amino acid cysteine 51 (Cys51) in the HPV-16 E6 protein sequence as referenced herein. Compounds of the invention covalently bond to the Cys51 residue of the HPV E6 protein. The region of E6AP that complexes with HPV E6 contains an HPV E6 binding motif with the consensus sequence LxxLL, where L is leucine and x is any amino acid that folds within an α-helix. The LxxLL motif of E6AP recognizes and binds to the hydrophobic pocket formed by two zinc fingers and the linker helix of HPV E6. Thus, the E6AP binding pocket on HPV E6 acts as a "hot spot" for association with cellular proteins encoding the LxxLL motif. A subsequent conformational change in E6AP-bound E6 exposes a large p53 interaction surface to generate the E6•E6AP•p53 trimeric complex. The LxxLL motif thus stabilizes the conformation of E6, enabling the recruitment of the tumor suppressor p53 to bind to a cleft on E6. In this stable trimeric complex, the E6AP ligase is catalytically activated and/or is close enough to tag p53 with ubiquitin molecules for degradation by the ubiquitin-proteasome system. The ubiquitination and degradation of this tumor suppressor leaves the cell devoid of important functions of p53, such as apoptosis induction, cell cycle arrest, DNA damage sensing, and the suppression of tumorigenesis.

The effect can be reversed in HPV-driven tumor cells by reduced expression of HPV E6, which reactivates p53 expression and leads to senescence or apoptosis. Inhibiting HPV E6 is shown to restore wild-type p53 protein levels and function. However, inhibition of HPV E6 has achieved only partial success. The unique topography of the α-helix binding groove of HPV E6 is essential in maintaining strong polar contacts with the HPV E6 binding motif. The rim arginines R10, R55, R102, R129, and R131 form multiple hydrogen bonds with both backbone and side-chain atoms. However, rather than relying on electrostatic intermolecular interactions such as hydrogen-bonding and π-cation contacts, or ionic bonds as forming the basis for interaction with HPV E6, compounds of the invention specifically and covalently bind to the Cys51 amino acid residue of the E6AP binding pocket of the HPV E6 protein. This covalent bonding interferes with the activities of HPV E6 including its ability to interact with E6AP.

As distinguished from hydrogen-bonds and/or ionic bonds, a covalent bond, as understood by persons skilled in the art, is a chemical bond wherein two or more atoms share one or more electron pairs. Protein-ligand binding typically occurs by intermolecular forces such as ionic bonds, hydrogen bonds, and Van der Waals forces. Therefore, measurably irreversible covalent bonding between a ligand and a target molecule is atypical. As discussed above, the E6AP binding pocket on HPV E6 acts as a "hot spot" for association with cellular proteins encoding the LxxLL motif. The compounds disclosed herein covalently bind within this pocket, or "hot spot" in HPV E6 and irreversibly block its interactions with E6AP. This also interferes with other binding partners that encode the HPV E6 binding motif.

Compounds of the invention form covalent bonds with the Cys51 amino acid residue of an HPV E6 protein such that the compound prevents E6AP binding and interferes with p53 ubiquitination and degradation. Without being bound to a specific pathway, in some embodiments of the invention, compounds of the invention covalently bond to one or more amino acids of an HPV E6 protein such that the compound inactivates HPV E6 and disrupts the protein-protein interactions that lead to oncogenicity. Without limitation, compounds of the invention may covalently bond with amino acid residues of any of the high-risk HPV types, including HPV-16 and HPV-18. For example, in specific embodiments of compounds disclosed herein, the compounds include an acrylamide substituent. Thus, covalent bonding of the compounds to the Cys51 residue of the HPV-16 E6 protein occurs via this acrylamide substituent.

Aspects of the invention provide compounds that form a covalent bond with the Cys51 amino acid residue in the HPV E6 protein, thereby preventing binding of another protein in the binding pocket. A binding pocket is a cavity on the surface or interior of a protein that possesses suitable properties for binding a ligand (e.g. a substance that forms a complex with a biomolecule to serve a biological purpose). In protein-ligand binding, the ligand is usually a molecule which produces a signal by binding to a site on a target protein, typically resulting in a change of conformational isomerism of the target protein. The set of amino acid residues around a binding pocket determines its physicochemical characteristics and, together with its shape and location in a protein, defines its functionality. Residues outside the binding site can also have a long-range effect on the properties of the binding pocket. Therefore, the binding site may be a region on the HPV E6 protein that binds with specificity to a ligand such that the compound covalently bonded to the binding pocket disrupts this specific binding and any associated conformational changes.

In another aspect, the invention provides a formulation comprising a compound that forms a covalent bond with a Cys51 residue in a human papilloma virus 16 E6 protein, thereby preventing binding of the HPV E6 protein to an E6AP protein. The compositions and compounds may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Formulations of the invention may be administered by a suitable route of delivery, such as oral, parenteral, intravenous, subcutaneous injection, rectal, nasal, topical, or ocular routes, or by inhalation.

Formulations of the invention also may comprise a pharmaceutically-acceptable adjuvant, diluent or carrier. Thus, the formulation may generally include a composition comprising the compound and other components, such as, for example, one or more pharmaceutically acceptable carriers, adjuvants, and/or vehicles appropriate for the particular route of administration for which the composition is to be employed. In some embodiments, the carrier, adjuvant, and/or vehicle is suitable for injection (via a needle for example) for intravenous, intramuscular, intraperitoneal, transdermal, or subcutaneous administration, as well as a consumable, or spray for related oral and inhalant administrations. The adjuvant may be, for example, aluminum, lipids, nucleic acids, or polyethylene glycol. Further, the formulation may be provided in a nanoparticle for targeted delivery.

One preferred formulation is a topical formulation for administration to areas of treatment such as the cervix, anus, or oropharynx. For topical applications, the compounds of the present invention are preferably formulated as creams, ointments, lotions, gels, or a similar vehicle suitable for topical administration. For topical administration, the inventive compounds may be mixed with a pharmaceutical carrier at a concentration of about 0.1% to about 10% of drug to vehicle. Additionally or alternatively, a mode of administering the agents of the invention may utilize a patch formulation to effect transdermal delivery.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin or olive oil.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compounds in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring and coloring agents, may also be present.

The formulations may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol or sucrose. Such formulations may also contain a demulcent, a preservative, and agents for flavoring and/or coloring. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

In another aspect, the invention provides a method for treating an HPV infection, the method comprising the step of delivering a formulation comprising a compound that forms a covalent bond with the Cys51 amino acid residue in a human papilloma virus 16 HPV E6 protein, thereby preventing binding of the HPV E6 protein to an E6AP protein.

Formulations of the invention may be delivered orally, transdermally, topically, subcutaneously, intramuscularly, or intravenously. Such formulations may be solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Formulations of the invention may be administered by a suitable route of delivery, such as oral, parenteral, intravenous, subcutaneous injection, rectal, nasal, topical, or ocular routes, or by inhalation.

In addition, formulations of the invention may comprise a pharmaceutically-acceptable adjuvant, diluent or carrier. Thus, the formulation may generally include a composition comprising the compound and other components, such as, for example, one or more pharmaceutically acceptable carriers, adjuvants, and/or vehicles appropriate for the particular route of administration for which the composition is to be employed. In some embodiments, the carrier, adjuvant, and/or vehicle is suitable for injection (via a needle for example) for intravenous, intramuscular, intraperitoneal, transdermal, or topical administration, as well as a consumable, or spray for related oral and inhalant administrations. The adjuvant may be, for example, aluminum, lipids, nucleic acids, or polyethylene glycol. Further, the formulation may be provided in a nanoparticle for targeted delivery.

Compounds

The present disclosure is directed to compositions, compounds, formulations, and methods for treating Human Papillomavirus (HPV) infections by covalently bonding to the Cys51 amino acid residue in the E6AP binding pocket of the HPV E6 protein. Particularly, compounds according to the invention covalently bind to amino acid residues of the E6AP binding pocket of HPV E6 protein and interfere with the activities of HPV E6, including its ability to interact with E6AP. Abrogation of HPV E6 activity has been found to lead to growth arrest of HPV-infected cells and/or cell death of HPV cervical cancer cell lines.

The invention provides examples of compounds that form a covalent bond with the Cys51 residue within the E6AP binding pocket in human papilloma virus (HPV) E6 protein, thereby preventing binding of the E6 protein to an E6AP protein. Preferred compounds of the invention comprise an acrylamide substituent or warhead. Thus, in certain embodiments, covalent bonding of the compounds of the invention to the Cys51 residue of the HPV-16 E6 protein occurs via the acrylamide substituent.

Compounds that covalently bind at Cys51 are useful in methods of disease management and treatment, such as inhibition or prevention of HPV, such as HPV E6. Any compound that covalently binds at Cys51 is useful in the invention. Provided below are exemplary compounds that covalently bind at Cys51 and block the E6 interaction with E6AP, and thereby restore p53 functions in HPV-infected cells.

In one example, the present disclosure is directed to methods for reducing HPV, (e.g., reducing HPV E6 levels, reducing the total number of infectious particles or reducing the number of infected cells), ameliorating HPV, e.g., HPV E6, and preventing an HPV infection in a subject in need thereof by administering one or more of the E6 covalent binding compounds disclosed herein.

Suitable subjects in need of treatment include subjects having (or suspected of having, based on exhibited symptoms or known exposure) an HPV infection. In one embodiment a subject known to be exposed to HPV, is administered a composition comprising an E6 binding compound of the present disclosure even prior to the subject demonstrating any symptoms of infection.

As the present invention is the first demonstration of covalent bonding at Cys51 in the E6AP protein numerous classes of compounds are contemplated herein. Below are provided exemplary compounds for use in the invention as exemplification of the covalent binding to Cys51.

Compound 1

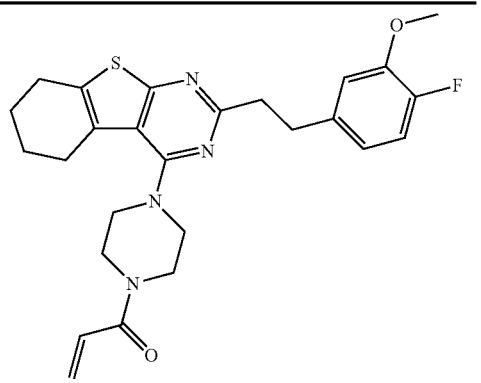

Compound 2

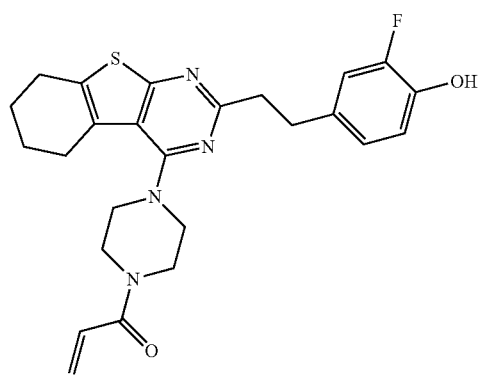 [SMILES: C=CC(=O)N1CCN(c2nc(CCc3ccc(O)c(F)c3)nc3sc4c(c23)CCCC4)CC1]

Compound 3

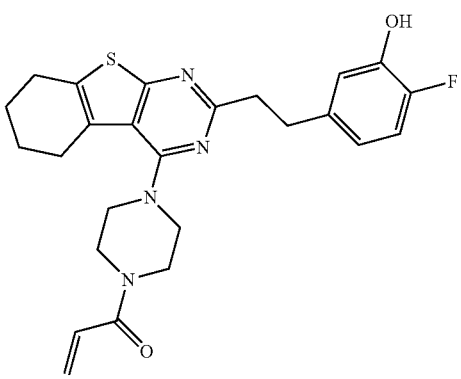 [SMILES: C=CC(=O)N1CCN(c2nc(CCc3ccc(F)c(O)c3)nc3sc4c(c23)CCCC4)CC1]

Compound 4

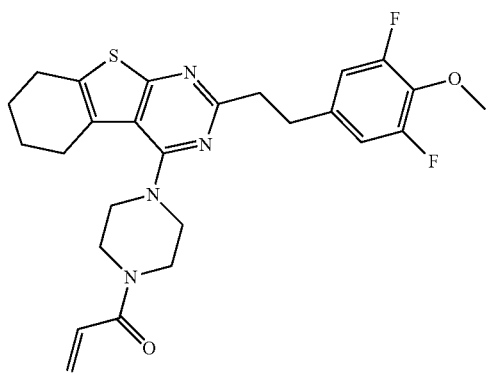 [SMILES: C=CC(=O)N1CCN(c2nc(CCc3cc(F)c(OC)c(F)c3)nc3sc4c(c23)CCCC4)CC1]

Compound 5

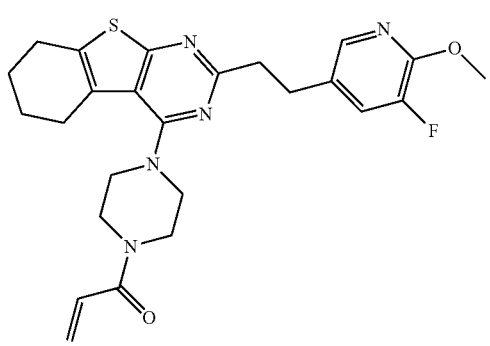 [SMILES: C=CC(=O)N1CCN(c2nc(CCc3cnc(OC)c(F)c3)nc3sc4c(c23)CCCC4)CC1]

Compound 6

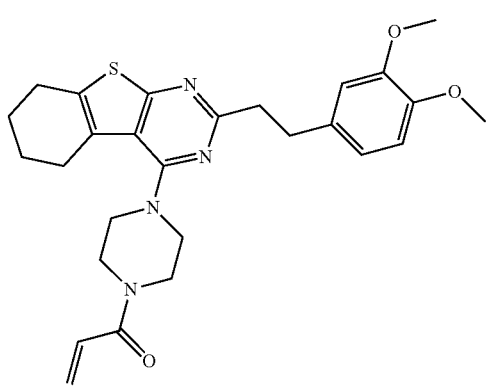 [SMILES: C=CC(=O)N1CCN(c2nc(CCc3ccc(OC)c(OC)c3)nc3sc4c(c23)CCCC4)CC1]

-continued

Compound 7
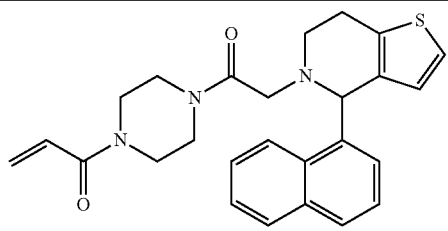

Compound 8
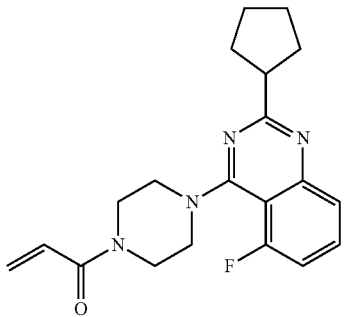 [SMILES: C=CC(=O)N1CCN(c2nc(C3CCCC3)nc3cccc(F)c23)CC1]

Compound 9
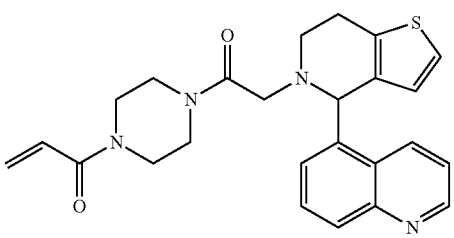 [SMILES: C=CC(=O)N1CCN(C(=O)CN2CCc3sccc3C2c2cccc3ncccc23)CC1]

Compound 10
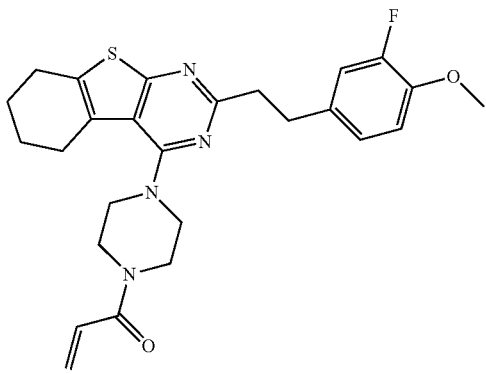 [SMILES: C=CC(=O)N1CCN(c2nc(CCc3ccc(OC)c(F)c3)nc3sc4c(c23)CCCC4)CC1]

Compound 11
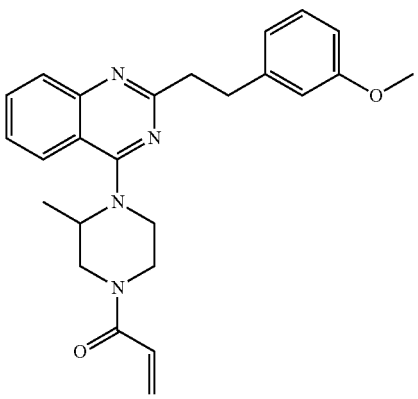 [SMILES: C=CC(=O)N1CCN(c2nc(CCc3cccc(OC)c3)nc3ccccc23)C(C)C1]

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, intravenous, subcutaneous injection, rectal, nasal, topical, or ocular routes, or by inhalation.

The pharmaceutical composition of the present disclosure can be used to ameliorating or preventing the worsening of existing HPV disease symptoms, preventing additional symptoms from occurring, ameliorating or preventing the underlying systemic causes of symptoms, inhibiting the disorder or disease, e.g., arresting the development of HPV infection and/or associated symptoms, relieving the disorder or disease, causing regression of the disorder or disease, relieving a condition caused by the disease or disorder, or stopping the symptoms of the disease or disorder.

Exemplary diseases include but are not limited to HPV infections of the vagina, cervix, perineum, rectum, anus, penis, vulva, vagina, skin, and oropharynx. These may be subclinical and detected by ultrasensitive molecular diagnostic tests. Diseases includes histologically benign infected epithelium, pre-malignant and dysplastic lesions, carcinoma-in-situ, invasive cancer, and metastatic cancers induced by HPV.

Examples

FIGS. 2A through 13B show the whole protein mass spectra of the HPV-16 E6 protein under exposure to a control compound vehicle (DMSO) or any of compounds 1-11. In order to show that the mass shift induced by compounds 1-11 is due to binding at Cys 51, each Figure shows the mass spectrogram of the mutant C51S (cysteine 51 replaced by serine) HPV-16 E6 protein as well. The mass shift of the molecular mass of each compound demonstrates those compounds are covalently bonded to the Cys51 of the E6 protein.

Figure 2B:
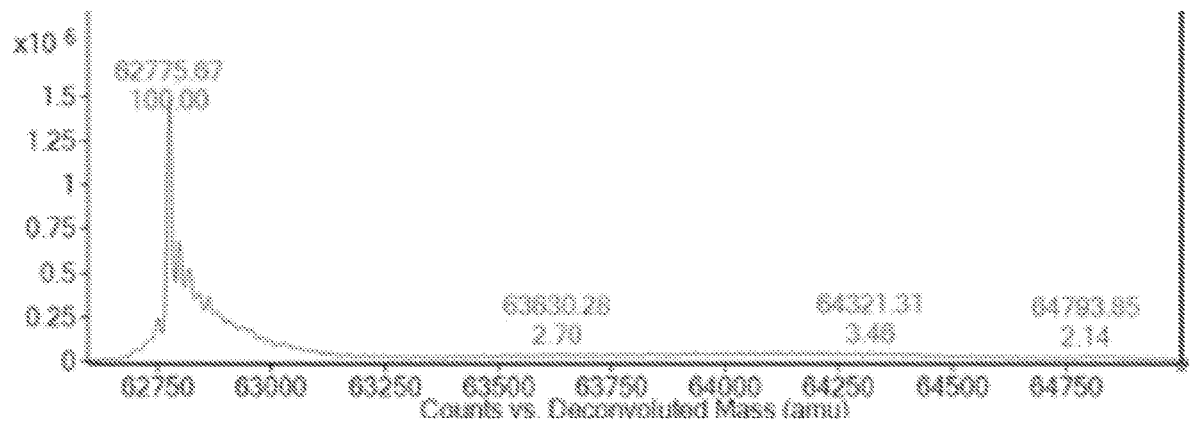
Figure 3A:
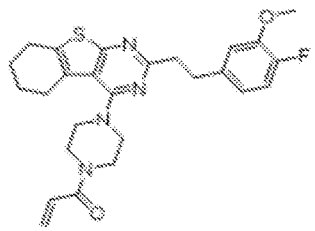
FIGS. 3A and 3B show the mass shift of the HPV-16 E6 protein upon exposure to Compound 1 with Cys51 (FIG. 3A) and the lack of mass shift with exposure of Compound 1 to the C51S protein (FIG. 3B).
Figure 3A:
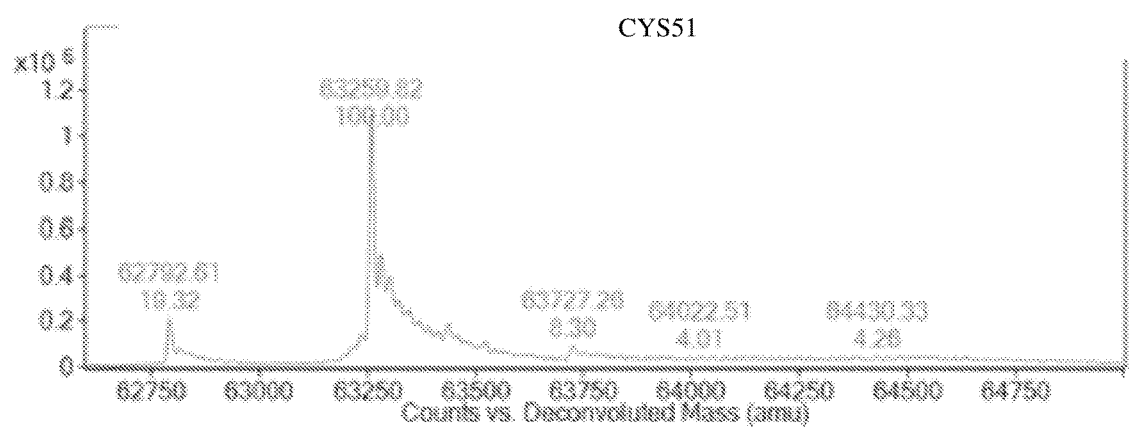
Figure 3B:
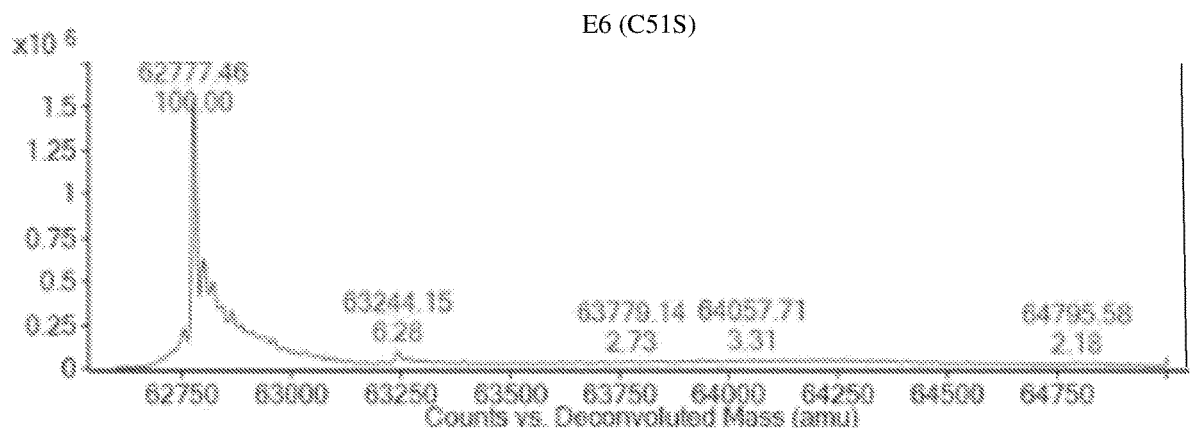
Figure 4A:
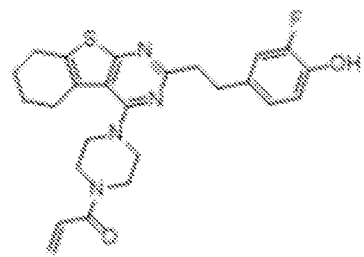
FIGS. 4A and 4B show the mass shift of the HPV-16 E6 protein upon exposure to Compound 2 with Cys51 (FIG. 4A) and the lack of mass shift with exposure of Compound 2 to the C51S protein (FIG. 4B).
Figure 4A:
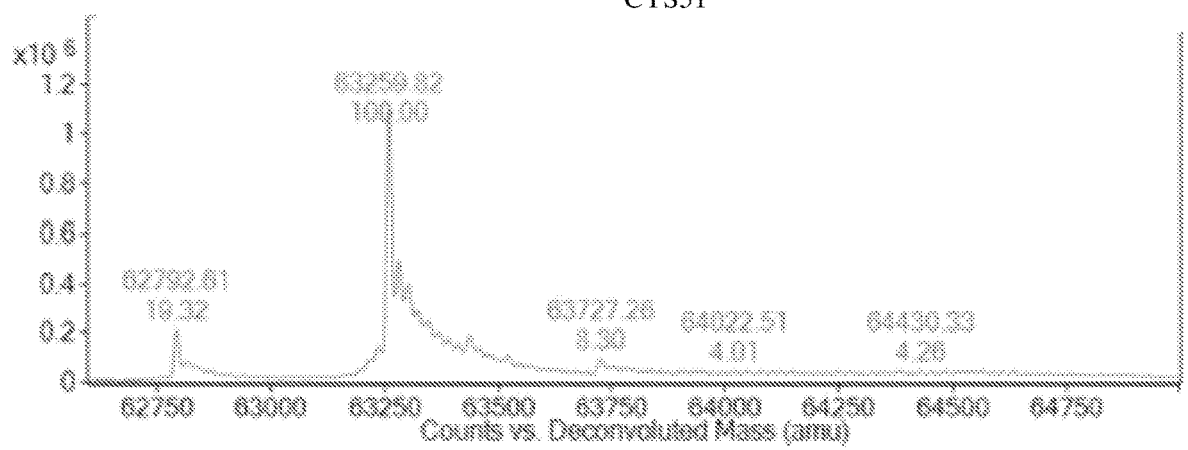
Figure 4B:
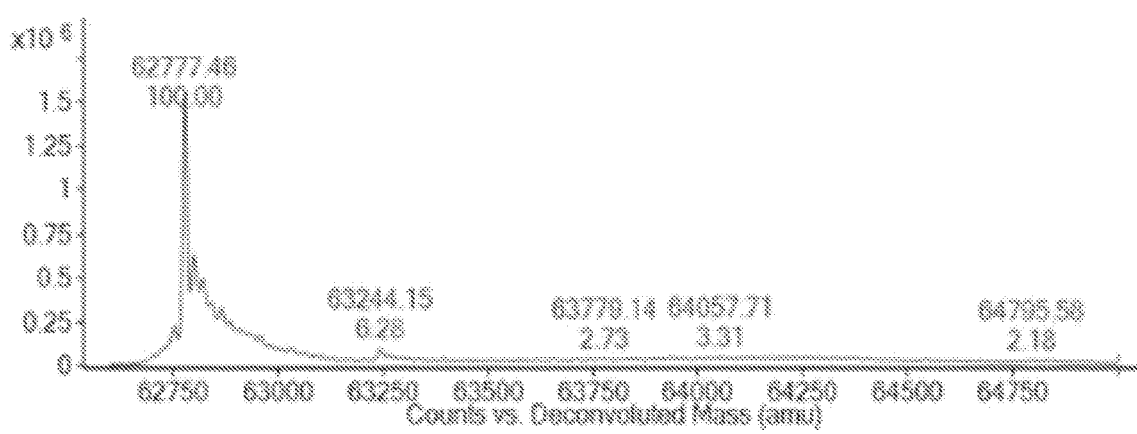
Figure 5A:
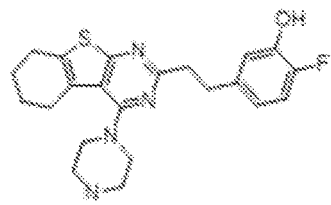
FIGS. 5A and 5B show the mass shift of the HPV-16 E6 protein upon exposure to Compound 3 with Cys51 (FIG. 5A) and the lack of mass shift with exposure of Compound 3 to the C51S protein (FIG. 5B).
Figure 5A:
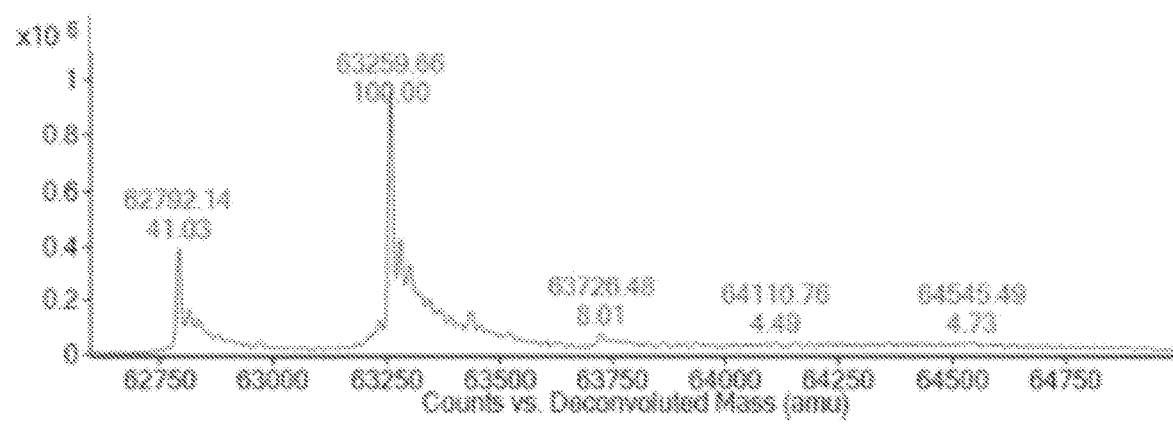
Figure 5B:
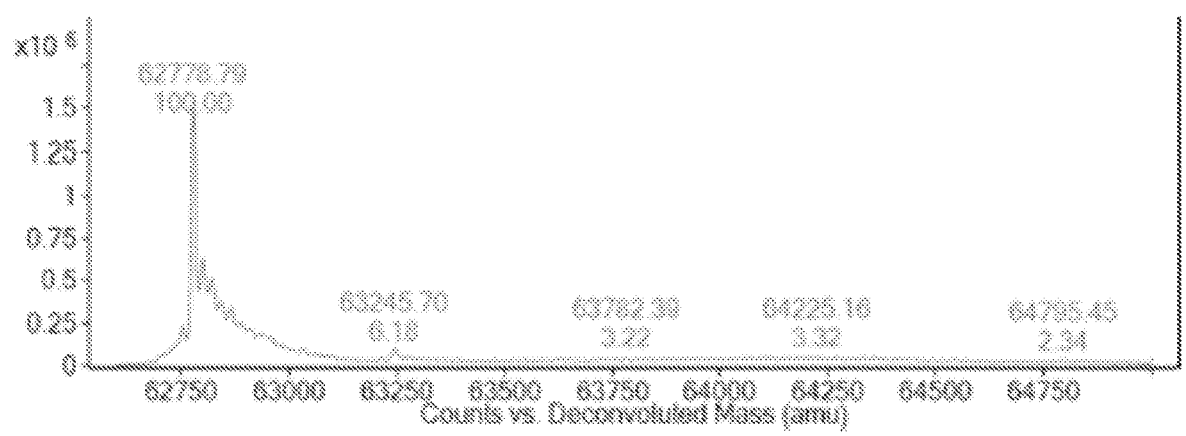
Figure 6A:
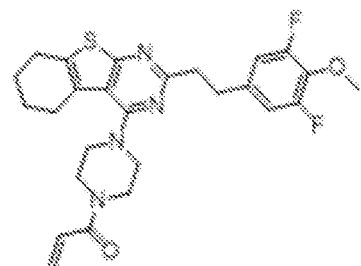
FIGS. 6A and 6B show the mass shift of the HPV-16 E6 protein upon exposure to Compound 4 with Cys51 (FIG. 6A) and the lack of mass shift with exposure of Compound 4 to the C51S protein (FIG. 6B).
Figure 6A:
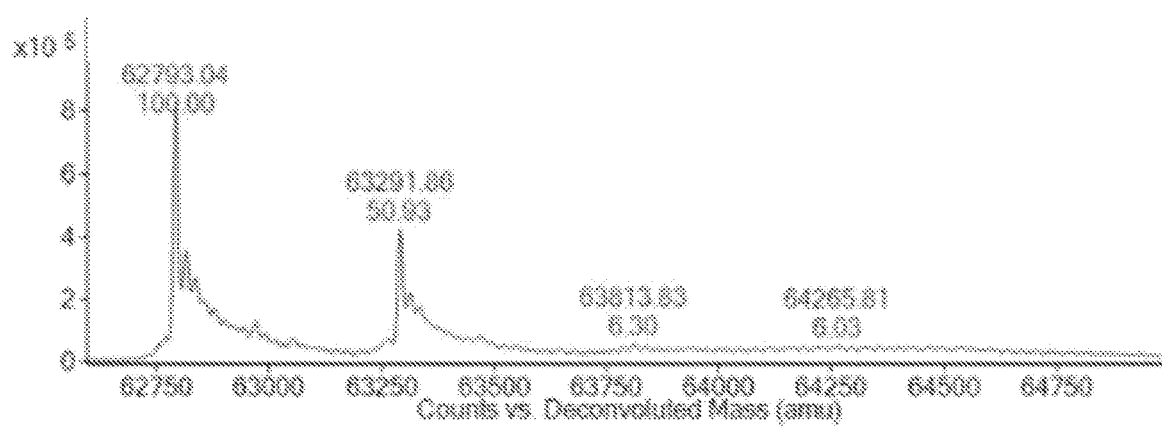
Figure 6B:
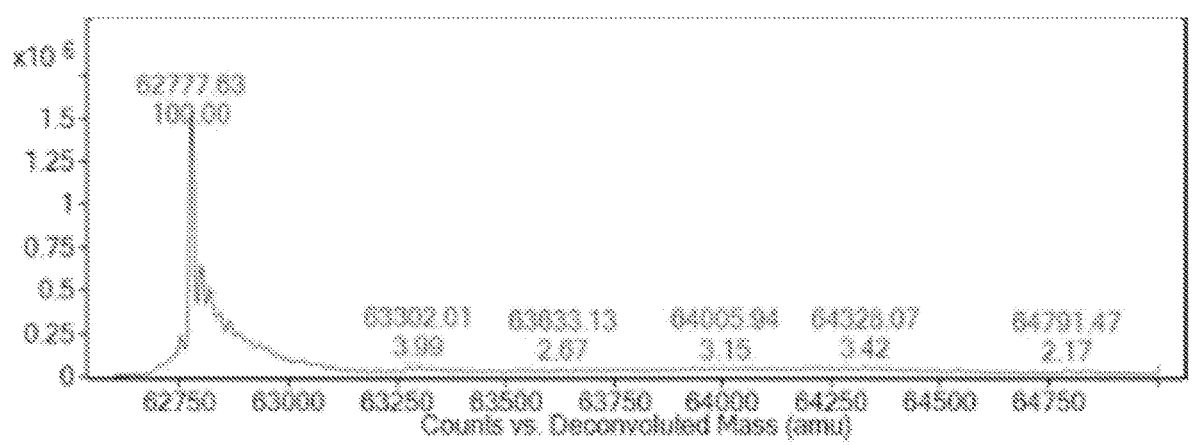
Figure 7A:
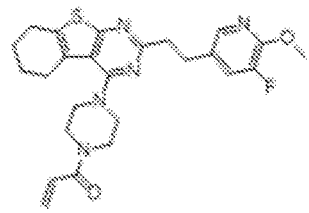
FIGS. 7A and 7B show the mass shift of the HPV-16 E6 protein upon exposure to Compound 5 with Cys51 (FIG. 7A) and the lack of mass shift with exposure of Compound 5 to the C51S protein (FIG. 7B).
Figure 7A:
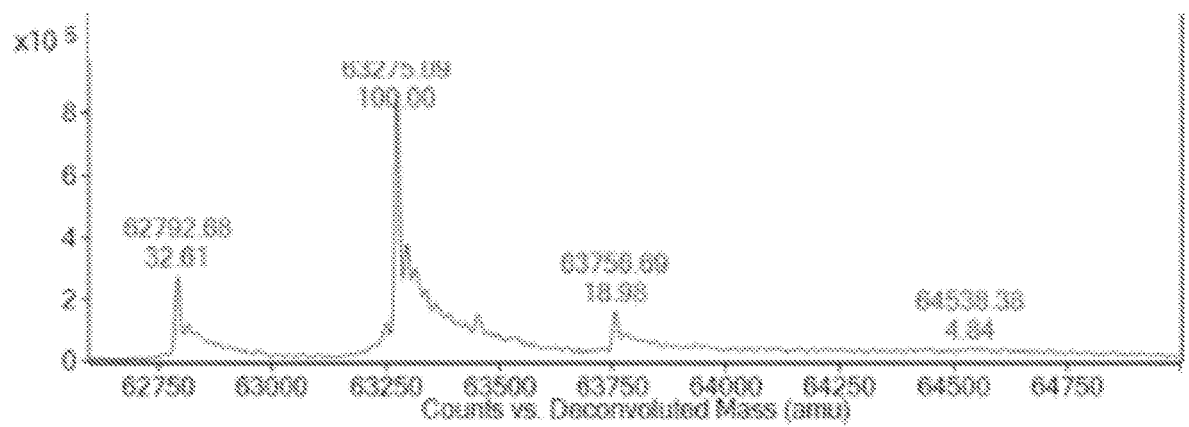
Figure 7B:
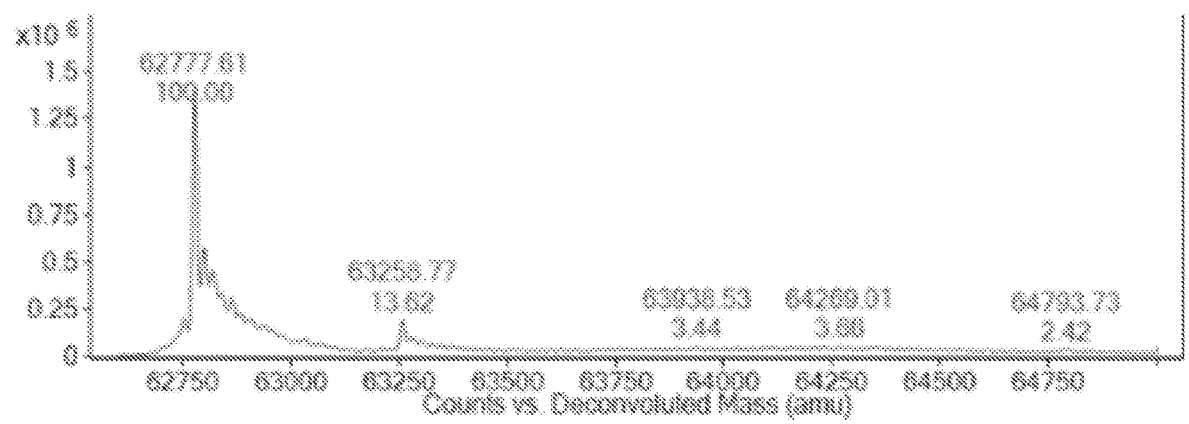
Figure 8A:
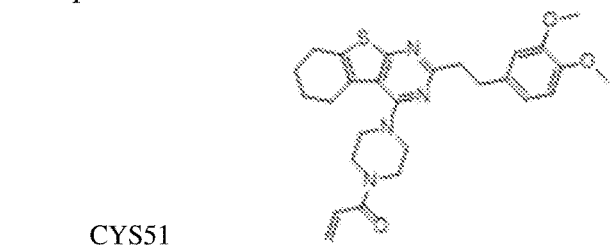
FIGS. 8A and 8B show the mass shift of the HPV-16 E6 protein upon exposure to Compound 6 with Cys51 (FIG. 8A) and the lack of mass shift with exposure of Compound 6 to the C51S protein (FIG. 8B).
Figure 8A:
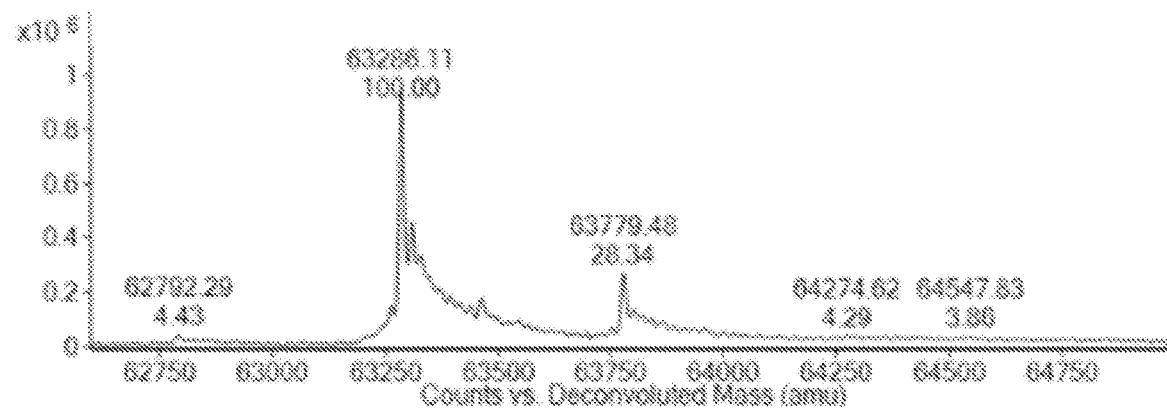
Figure 8B:
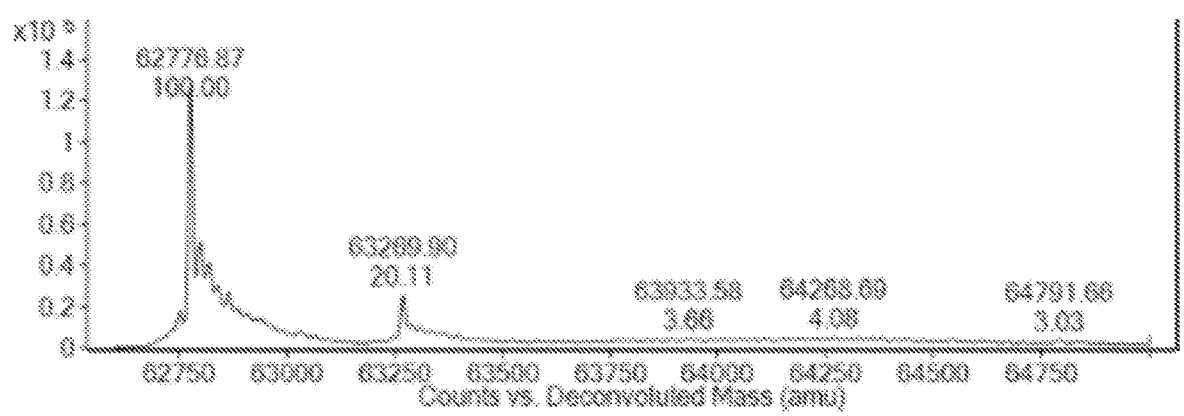
Figure 9A:
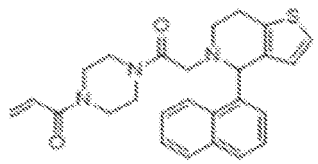
FIGS. 9A and 9B show the mass shift of the HPV-16 E6 protein upon exposure to Compound 7 with Cys51 (FIG. 9A) and the lack of mass shift with exposure of Compound 7 to the C51S protein (FIG. 9B).
Figure 9A:
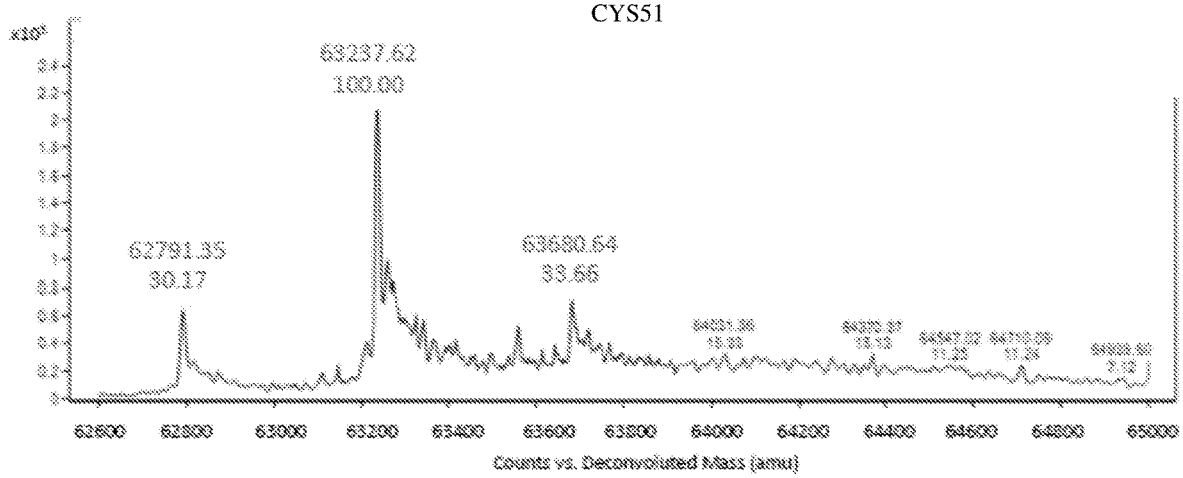
Figure 9B:
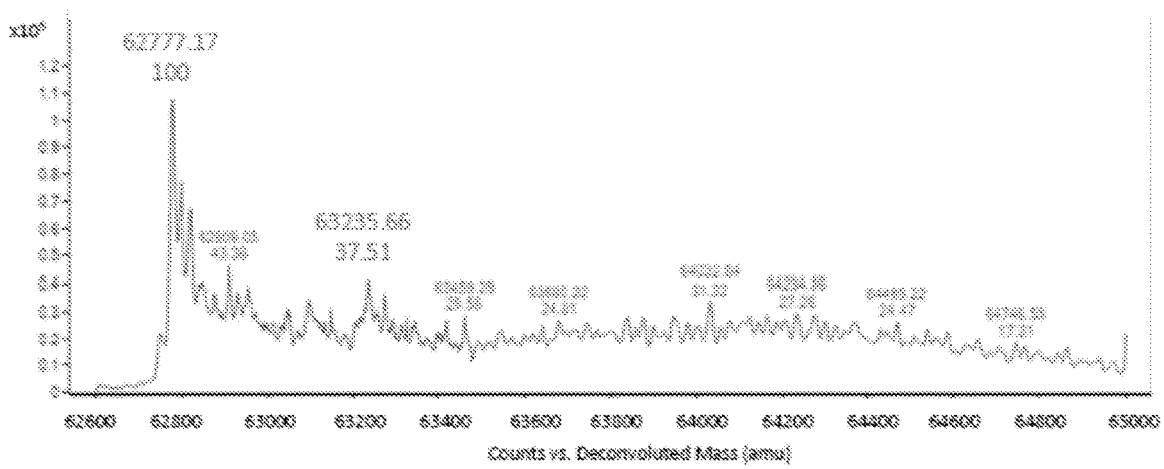
Figure 10A:
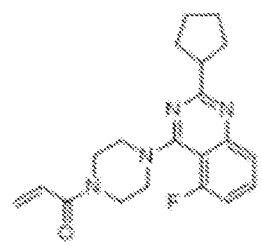
FIGS. 10A and 10B show the mass shift of the HPV-16 E6 protein upon exposure to Compound 8 with Cys51 (FIG. 10A) and the lack of mass shift with exposure of Compound 8 to the C51S protein (FIG. 10B).
Figure 10A:
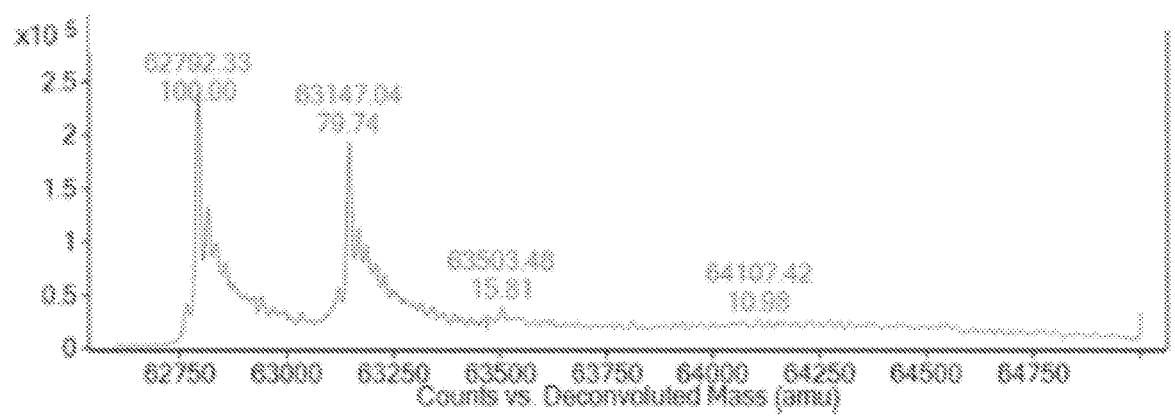
Figure 10B:
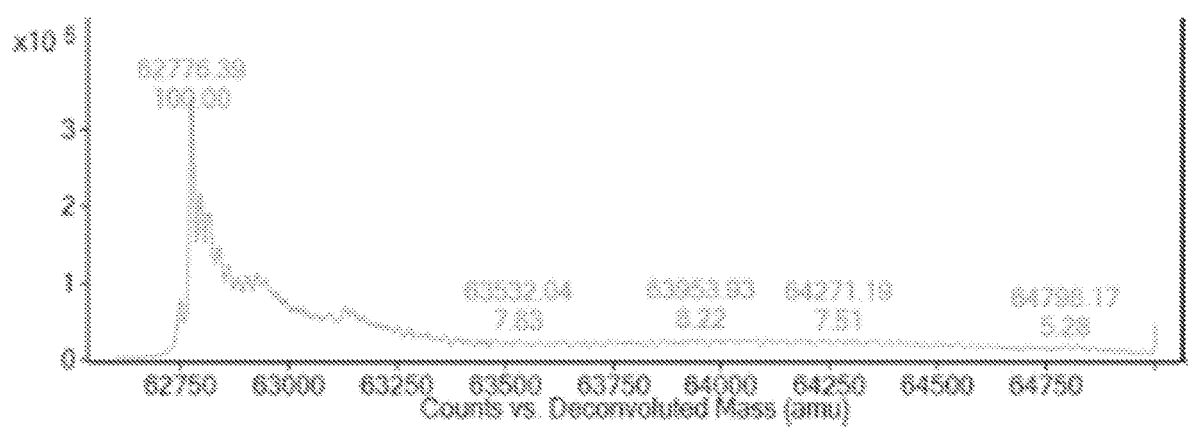
Figure 11A:
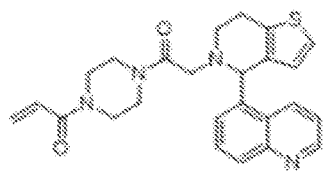
FIGS. 11A and 11B show the mass shift of the HPV-16 E6 protein upon exposure to Compound 9 with Cys51 (FIG. 11A) and the lack of mass shift with exposure of Compound 9 to the C51S protein (FIG. 11B).
Figure 11A:
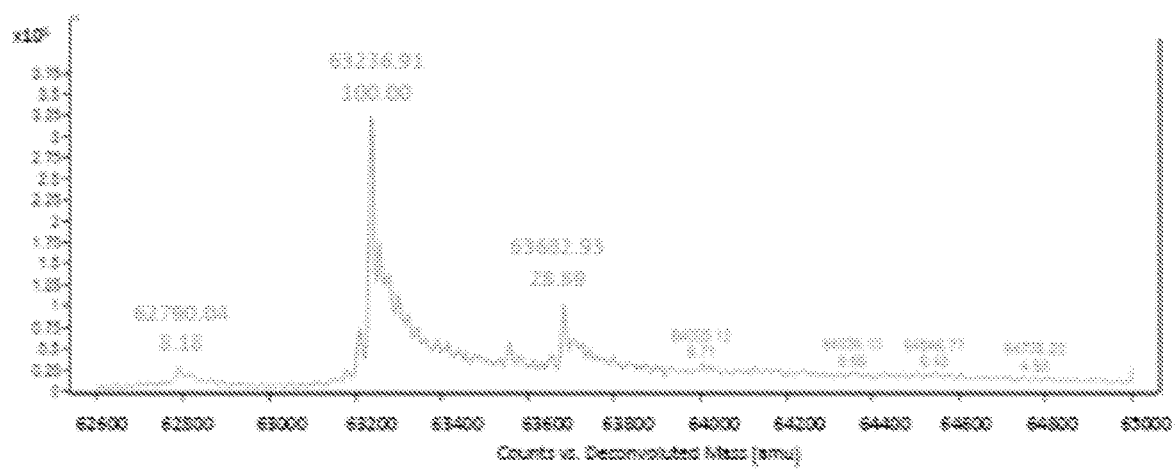
Figure 11B:
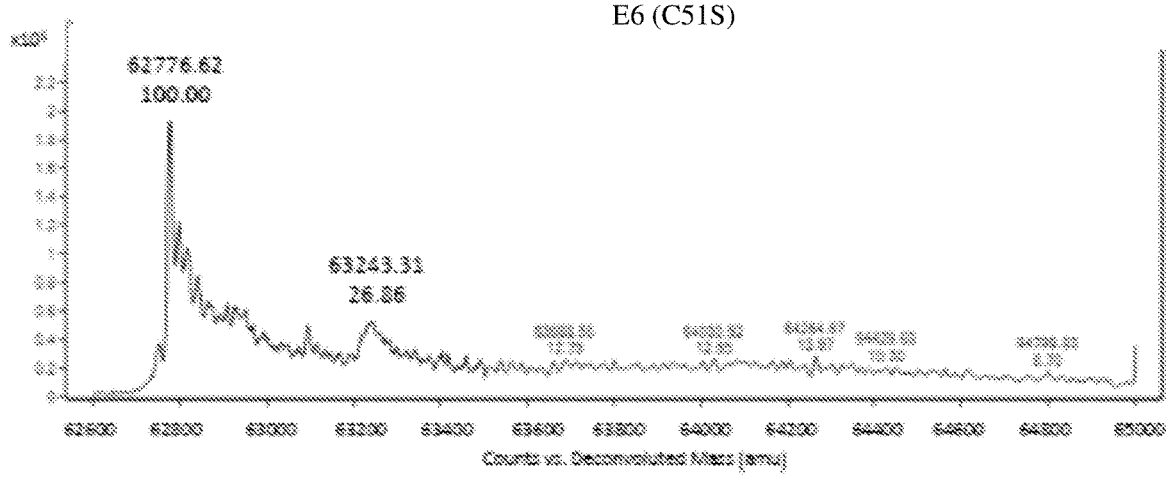
Figure 12A:
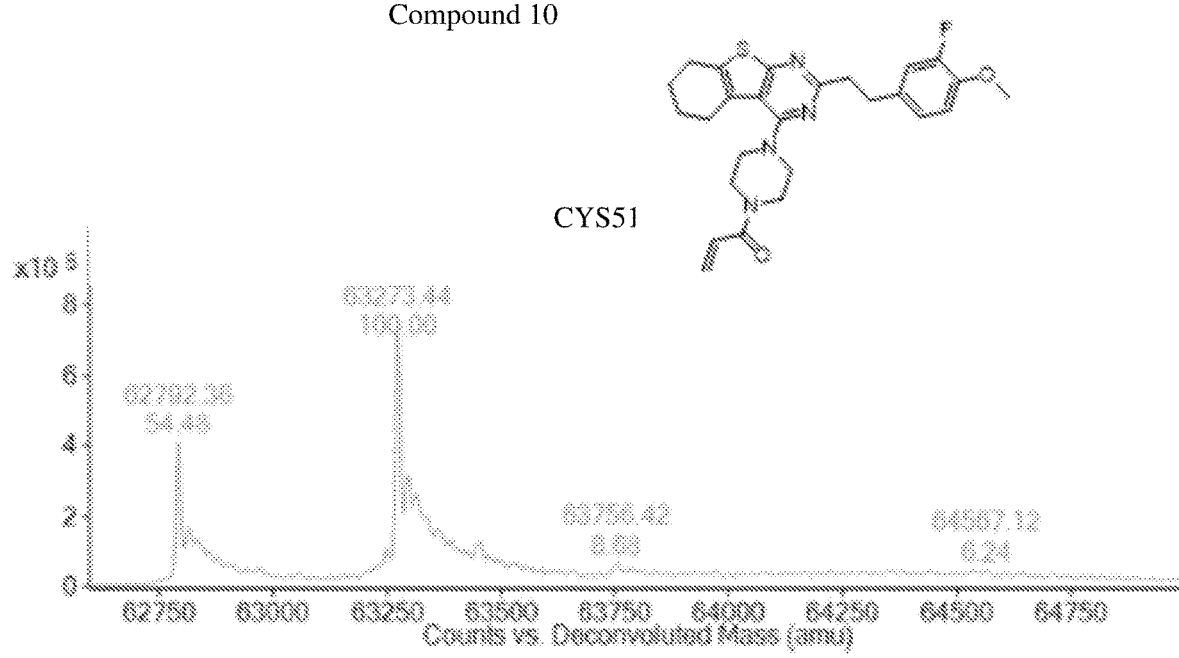
FIGS. 12A and 12B show the mass shift of the HPV-16 E6 protein upon exposure to Compound 10 with Cys51 (FIG. 12A) and the lack of mass shift with exposure of Compound 10 to the C51S protein (FIG. 12B).
Figure 12B:
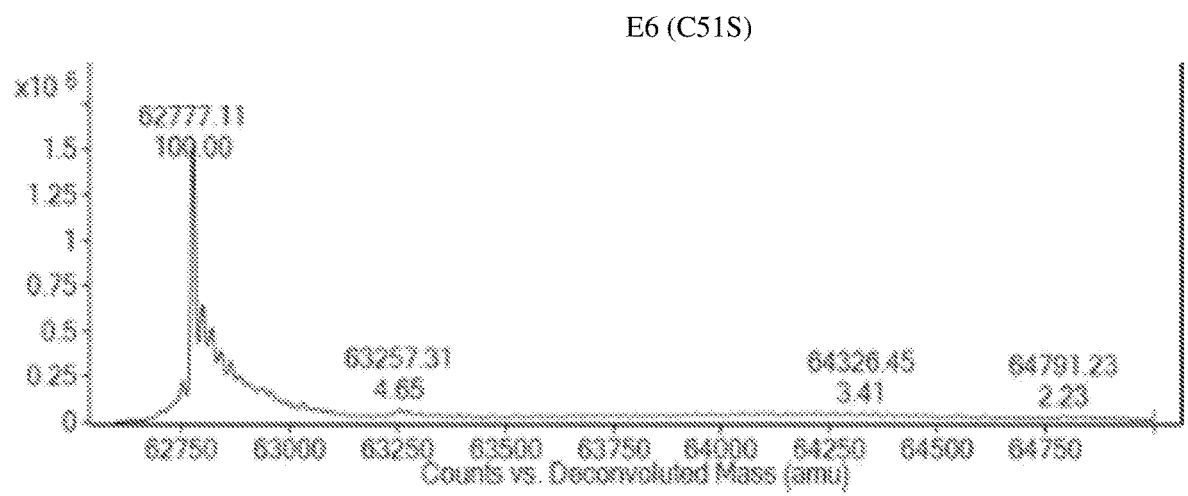
Figure 13A:
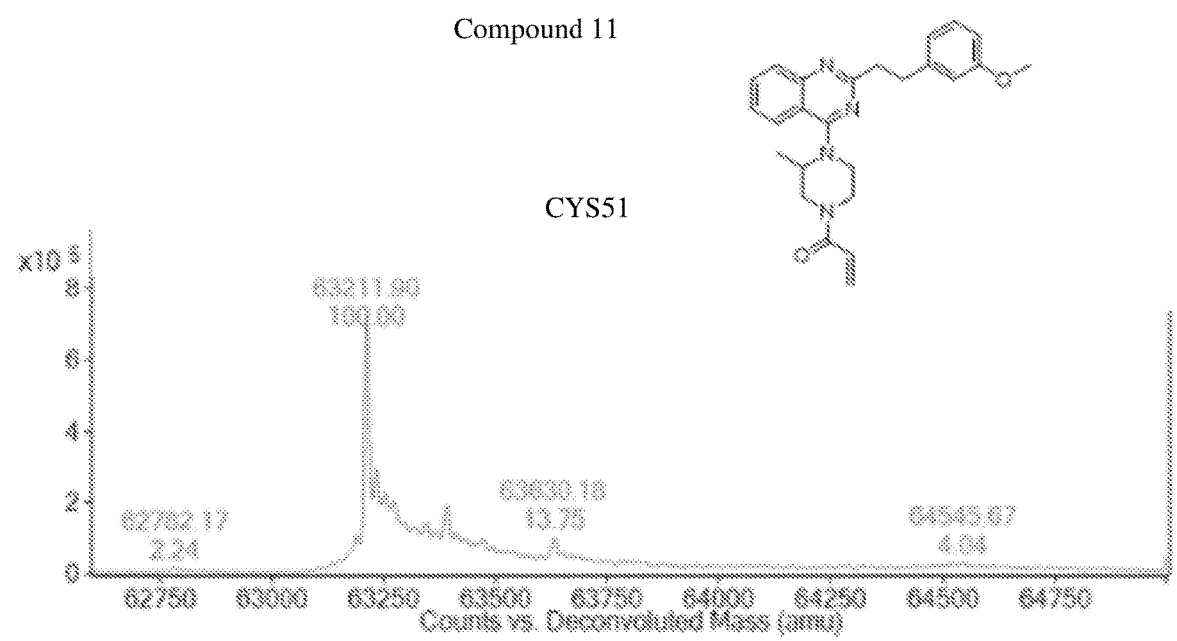
FIGS. 13A and 13B show the mass shift of the HPV-16 E6 protein upon exposure to Compound 11 with Cys51 (FIG. 13A) and the lack of mass shift with exposure of Compound 11 to the C51S protein (FIG. 13B).
Figure 13B:
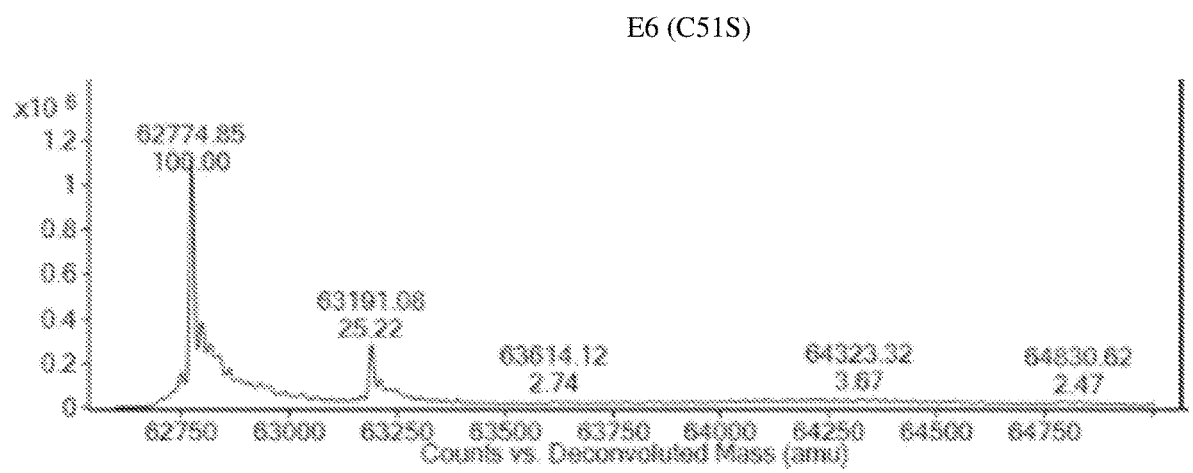

FIGS. 2A and 2B illustrate the mass spectrum of E6 before reaction with one of the test compounds. FIGS. 3A through 13B illustrate a mass shift of the whole protein HPV-16 E6 protein when covalently bound at Cys51 to one of the test compounds. That mass shift was not detected using an HPV-16 E6 protein in which Cys51 was replaced by a serine (C55) because serine, while a very conservative amino acid change, cannot make a covalent bond to the acrylamide in Compounds 1-11.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein.

The subject matter herein contains important information, exemplification, and guidance that can be adapted to the practice of this invention in its various embodiments and equivalents thereof.

SEQUENCES

The following sequences may be referred to or used within the disclosure.

SEQ ID NO: 1
MFQDPQERPRKLPQLCTELQTTIHDIILECVYCKQQLLRREVYDFAFRD
LCIVYRDGNPYAVCDKCLKFYSKISEYRHYCYSLYGTTLEQQYNKPLCD
LLIRCINCQKPLCPEEKQRHLDKKQRFHNIRGRWTGRCMSCCRSSRTRR
ETQL

---

---

What is claimed is:

1. A compound that forms a covalent bond with a Cysteine residue in the E6AP binding pocket of a human papillomavirus E6 protein, thereby preventing interaction of the HPV E6 protein with an E6AP protein.

2. The compound of claim 1, wherein said compound binds to Cysteine 51 in the HPV-16 E6 protein.

3. The compound of claim 1, wherein said compound contains an acrylamide that forms a covalent bond to a Cysteine in the E6AP binding pocket of a human papillomavirus E6 protein.

4. A formulation comprising the compound of claim 1.

5. The formulation of claim 4, comprising a pharmaceutically acceptable adjuvant, diluent or earner.

6. The formulation of claim 4, provided in a nanoparticle for targeted delivery.

7. A method for treating an HPV infection, dysplasia, or malignancy, the method comprising the step of delivering a formulation according to claim 5.

8. The method of claim 7, wherein said formulation is delivered orally, transdermally, topically, subcutaneously, intramuscularly, intralesionally or intravenously.

9. The method of claim 7, wherein the formulation is formulated for topical application to the cervix, anus, or pharynx.

10. The method of claim 8, wherein said formulation comprises an effective dose for transdermal delivery of about 0.01% to about 10% of the compound of claim 1.

11. The method of claim 8, wherein said formulation is a time-release formulation.

12. The method of claim 7, wherein said formulation inhibits E6AP binding to HPV E6 preventing ubiquitination of p53.

13. The formulation of claim 5, wherein the formulation further comprises a compound selected from the group consisting of fatty acids, glucose, amino acids, cholesterol, lipids, glycosides, alkaloids, and natural phenols.

* * * * *